(12) United States Patent
Jokes et al.

(10) Patent No.: US 6,455,002 B1
(45) Date of Patent: Sep. 24, 2002

(54) METHOD FOR WEIGHING SAMPLE TUBES, AND WORKSTATION

(75) Inventors: Ivan Jokes, Rüti (CH); Martin Rüdisser, Jona (CH); Fred Schinzel, Männedorf (CH)

(73) Assignee: Tecan Trading AG, Männedorf (CH)

( * ) Notice: Subject to any disclaimer, the term of this patent is extended or adjusted under 35 U.S.C. 154(b) by 0 days.

(21) Appl. No.: 09/438,792

(22) Filed: Nov. 12, 1999

(30) Foreign Application Priority Data

Nov. 17, 1998 (CH) .............................................. 2297/98

(51) Int. Cl.[7] .............................................. G01N 35/02
(52) U.S. Cl. .............................. 422/63; 422/38; 422/72; 494/16; 436/147
(58) Field of Search .............................. 422/63, 38, 72; 73/38, 434; 494/16; 436/147, 45, 48

(56) References Cited

U.S. PATENT DOCUMENTS

| | | | |
|---|---|---|---|
| 5,363,885 A | * | 11/1994 | McConnell et al. |
| 5,409,667 A | * | 4/1995 | Elson |
| 5,769,775 A | * | 6/1998 | Quinland et al. |
| RE36,341 E | * | 10/1999 | Howell |
| 6,056,924 A | * | 5/2000 | Jackson et al. |
| 6,060,022 A | | 5/2000 | Pang et al. |
| 6,210,571 B1 | * | 4/2001 | Zambias et al. |

* cited by examiner

*Primary Examiner*—Ana Fortuna
(74) *Attorney, Agent, or Firm*—Notaro & Michalos P.C.

(57) ABSTRACT

A workstation has a feed device (1) for sample tube racks (7), comprising a balance (17) in which the weight of individual sample tubes (6) is determined by a procedure in which the sample tube holder (7) is weighed in each case before and after removal of each sample tube (6) and the difference between the weights is determined. Removal is effected in each case by means of a gripper (23) of a transfer device (3) which then distributes the sample tubes (6) over sample tube buckets (22) in such a way that said buckets form pairs having approximately the same weights. With the aid of a receiving device (27) which is gripped by the gripper (23) and removed from a holder, the sample tube buckets (22) are picked up and introduced into a centrifuge (2). They are removed again after centrifuging and, after the receiving device (27) has been deposited in the holder, the individual sample tubes (6) are removed from the sample tube buckets (22) by the gripper and deposited on carriers (5) of a conveying device (4).

10 Claims, 5 Drawing Sheets

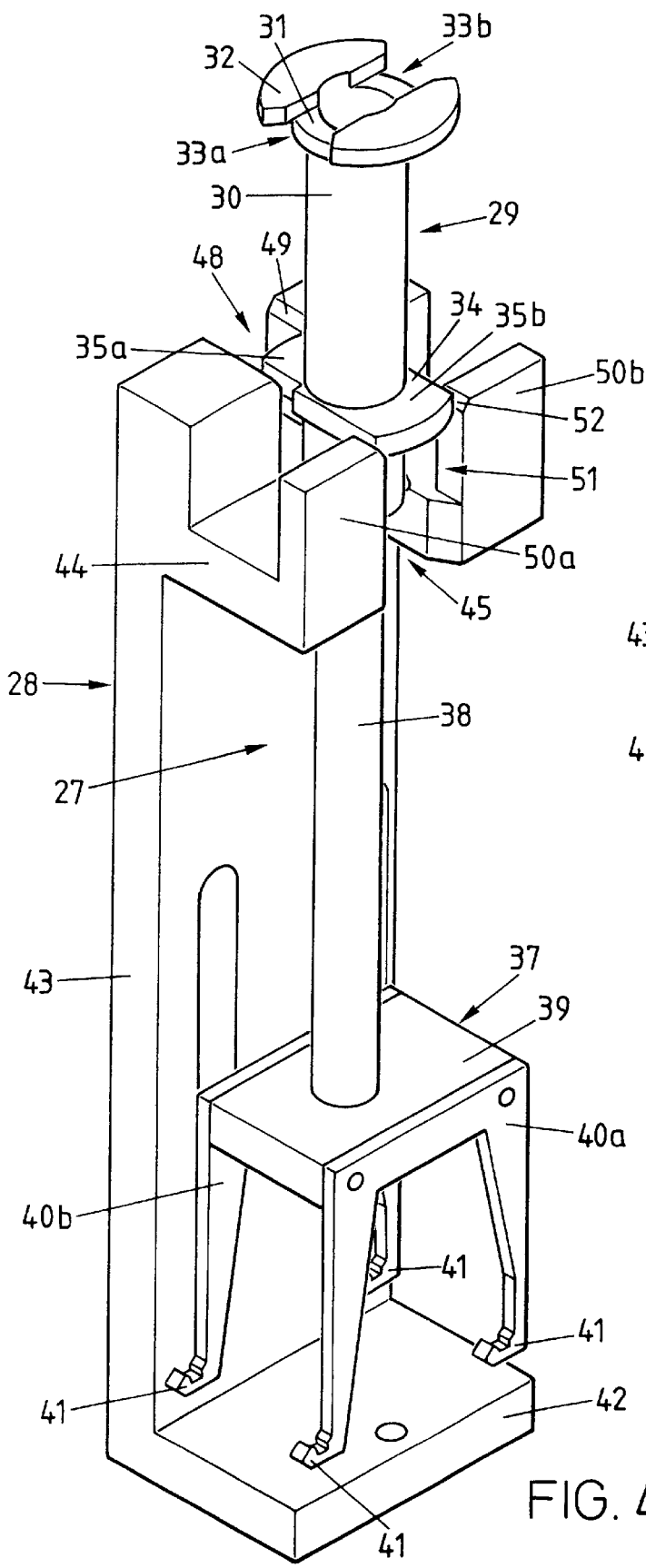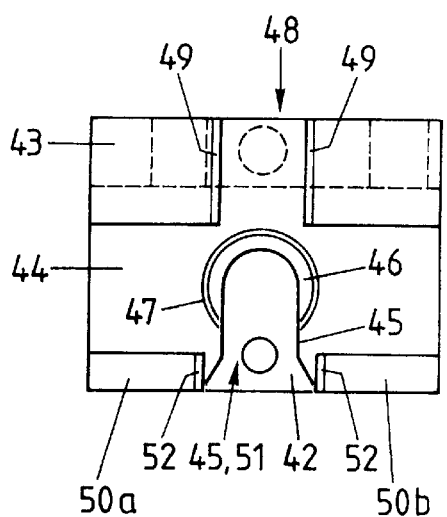
FIG. 4
FIG. 5

METHOD FOR WEIGHING SAMPLE TUBES, AND WORKSTATION

FIELD OF THE INVENTION

The invention relates to a method for weighing sample tubes which are delivered in a sample tube rack, as used especially for preparing for centrifuging samples in chemical, biological and medical laboratories, and a workstation as used in association with such and similar methods.

PRIOR ART

In the laboratory, it is often necessary to determine individually the weights of sample tubes, which are usually delivered in the form of several sample tubes in a sample tube rack. If, for example, the liquid samples are to be centrifuged, the sample tubes must be distributed over a plurality of sample tube buckets, usually four sample tube buckets, which are then introduced into the centrifuge. To limit the imbalance, the weights of sample tube buckets opposite one another may differ from one another by not more than a maximum value of, usually, between 15 g and 20 g.

WO-A-98/01 760 discloses a method of the generic type and a workstation of the generic type for carrying out said method. According to this publication, the weights of sample tubes are determined by removing them in succession from a sample tube rack and placing them by means of a transfer device in a sample tube bucket which is arranged on a balance. The weight of each sample tube is determined from the increase in the weight of the sample tube bucket caused by adding a sample tube. The sample tubes are distributed over sample tube buckets in such a way that the latter form pairs so that the total weights of the sample tube buckets belonging to one pair differ by not more than 10 g. In this method, the weight is not determined until after the addition of the sample tube, so that the weight determined cannot be used for controlling the addition of the sample tubes themselves, in particular their distribution over the sample tube buckets, according to the determined weights and for avoiding incorrect distributions from the outset. Errors have to be corrected subsequently by redistributing the sample tubes or by using balancing weights, which can result in considerable time losses.

GB-A-997 226 discloses a transport track having conveyor belts, with a balance which has a platform which can be raised and by means of which articles can be lifted off the transport track and their weight determined, whereupon they are set down again on the transport track by lowering the platform and are transported further. The device is not suitable for removing parts of articles and determining the weights of these parts.

U.S. Pat. No. 3,489,521 describes a workstation having a feed device for sample tube racks, comprising a feed track and a return track parallel to said feed track, both having conveyor belts, and comprising a transverse intermediate track which connects the feed track to the return track. It also has a centrifuge in which the sample tubes are centrifuged without prior weighing in the sample tube racks.

SUMMARY OF THE INVENTION

It is the object of the invention to simplify and to accelerate the weighing of the sample tubes in comparison with the known methods of the generic type. This object is achieved by the features in the characterizing clause of claim 1. In the method according to the invention, intermediate deposition of the sample tube whose weight is to be determined is unnecessary. It can be removed from the sample tube rack and brought directly, for example, to a sample tube bucket and deposited there. The determination of the weight causes no delay.

Furthermore, the workstation of the generic type is to be adapted in such a way that it is suitable for carrying out the method according to the invention and in particular substantially facilitates the feeding and weighing of sample tubes. This object is achieved by the features in the characterizing clause of claim 4. The workstation according to the invention permits simple feeding of the sample tube racks to the balance and convenient removal of individual sample tubes therefrom.

BRIEF DESCRIPTION OF THE DRAWINGS

The invention is explained in more detail below with reference to Figures which represent only one embodiment.

FIG. 4 shows a perspective view of parts of the transfer device according to the invention, FIG. 5 shows a plan view of one of the parts, shown in FIG. 4, of the transfer device according to the invention.

DESCRIPTION OF THE PREFERRED EMBODIMENTS

Figure 1:
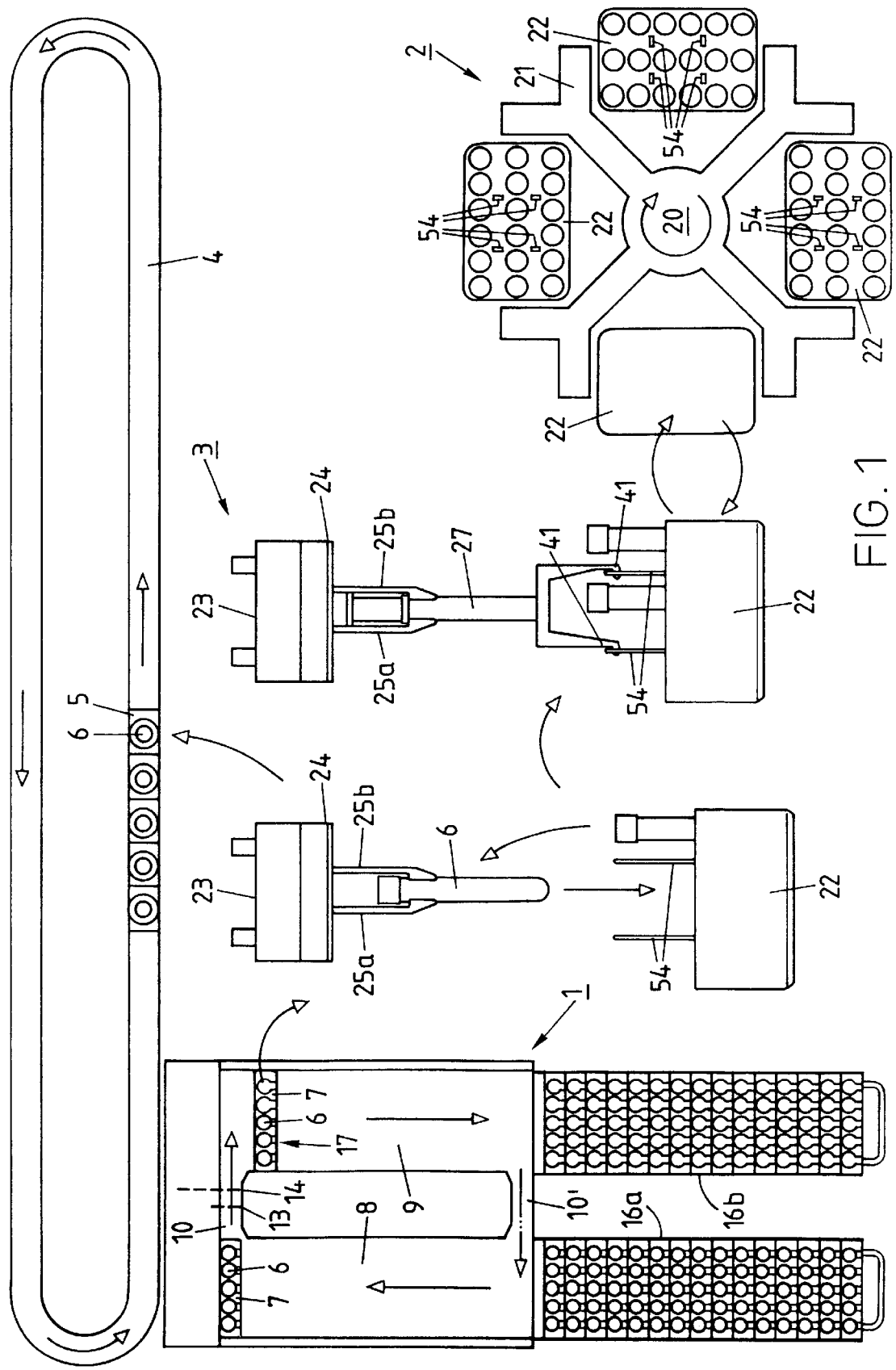
FIG. 1 shows a schematic overview of a workstation according to the invention and the sequence of the method according to the invention.

FIG. 1 shows the workstation comprising a feed device 1, a centrifuge 2 and a transfer device 3. Also present is a conveying device 4 which brings individual sample tubes 6 inserted in carriers 5 to other processing modules (not shown).

Figure 2:
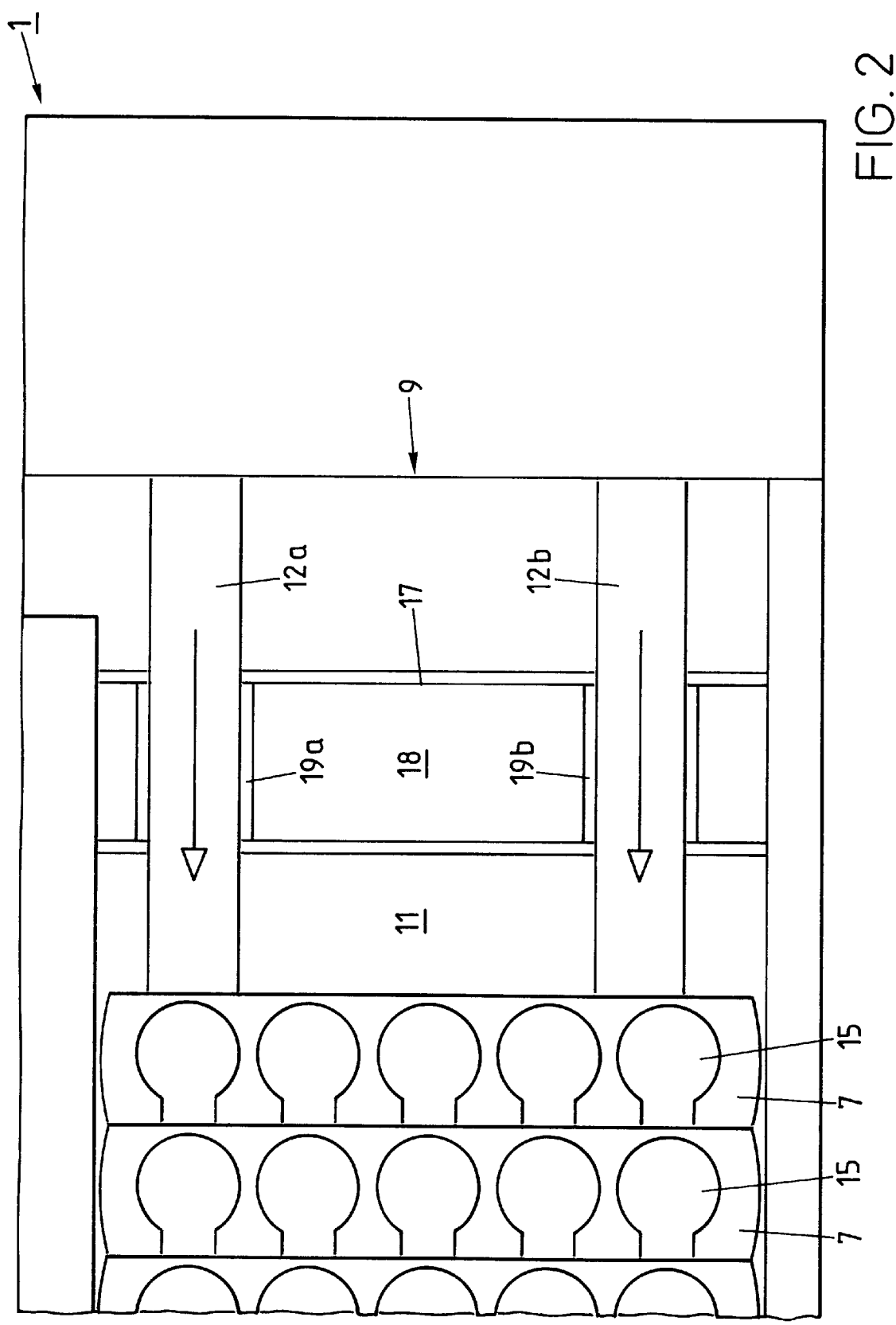
FIG. 2 shows a plan view of a part of a feed device according to the invention.

The feed device 1 is used for feeding sample tubes 6 which are delivered, usually in the form of several sample tubes but under certain circumstances also individually, in sample tube racks 7 to the workstation and also for checking and classifying them. It comprises a feed track 8 and a return track 9 which is arranged a small distance away from said feed track and parallel to it. The end of the feed track 8 is connected to the beginning of the return track 9 by a transverse intermediate track 10. As shown in FIG. 2 for the return track 9 as an example, the latter and the feed track 8 each have conveyor belts 12a,b arranged side by side and a distance apart and running over a baseplate 11. On the other hand, the intermediate track 10 has a lateral conveyor belt which engages cams in lateral recesses in the sample tube racks 7. On the opposite side, a height scanner 13 having two reflecting cells arranged at different heights and a bar code reader 14 are arranged side by side on the intermediate track 10. Moreover, a second transverse intermediate track 10' which connects the end of the return track 9 to the beginning of the feed track 8 can be provided.

The identically formed sample tube racks 7 each have a plurality of recesses 15 (FIG. 2)—five in the case shown— arranged one behind the other in a longitudinal direction and having laterally continuous vertical slots which serve for receiving sample tubes 6. They are delivered in a drawer 16a which contains a number of sample tube racks 7 which are arranged transversely one behind the other. The drawer 16a can be coupled to the feed device 1 at the entrance of the feed track 8. A further drawer 16b can likewise be coupled at the exit of the return track 9. While the first drawer 16a is oriented horizontally, the second drawer 16b slopes downward in an outward direction at an angle of about 15° to the horizontal.

Figure 3:
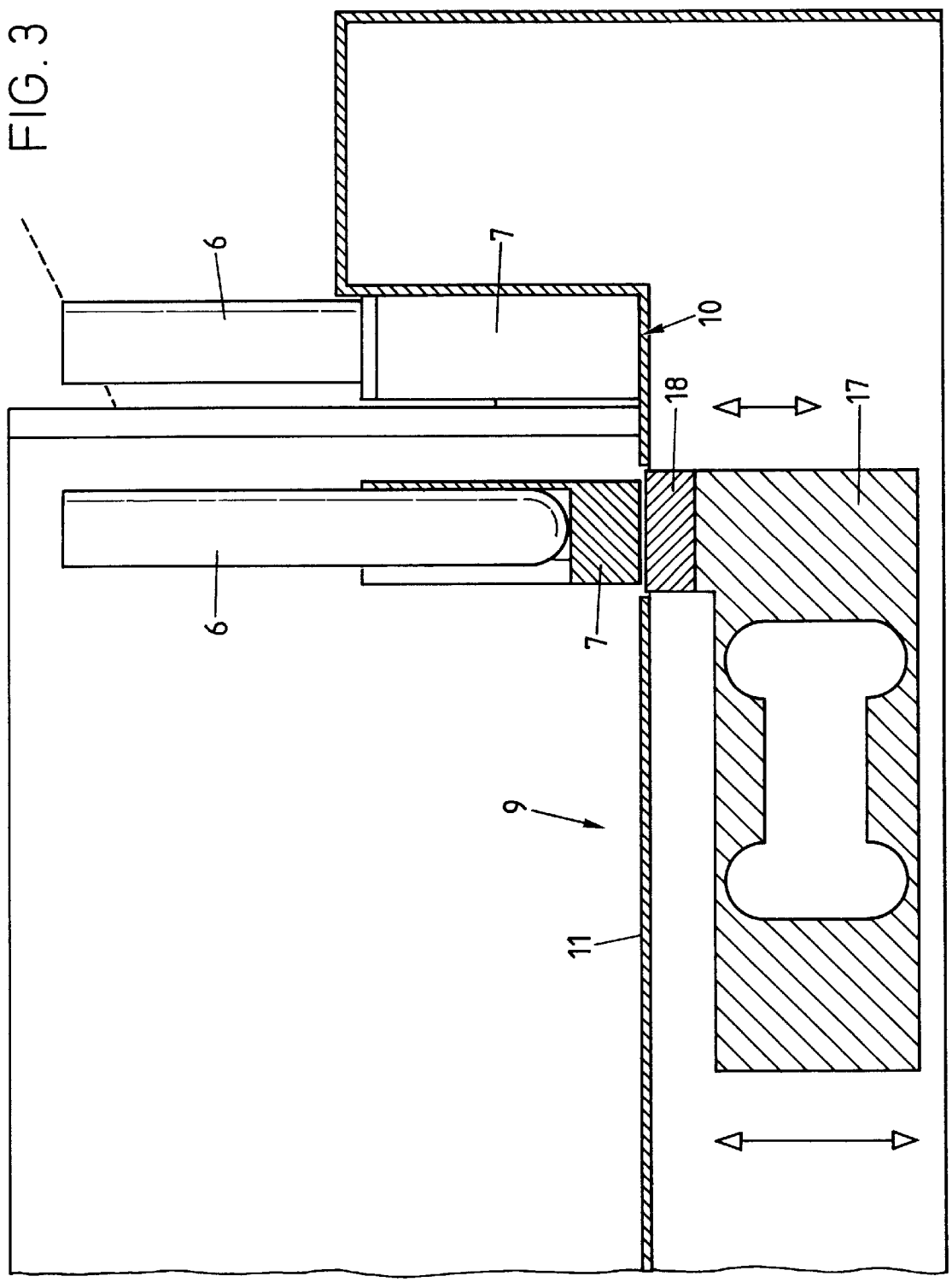
FIG. 3 shows a vertical longitudinal section through that part of the feed device according to the invention which is shown in FIG. 2.

A balance 17 which comprises a parallelogram support with wire strain gauge is arranged at the entrance of the return track 9, below the baseplate 11, with a platform 18 (FIGS. 2, 3) which essentially fills an opening in the baseplate 11, which opening extends over the total width of the return track 9. The platform 18 has, on its upper side, two recesses 19a,b which are continuous in the longitudinal direction of the return track 9. The balance 17 can be raised from an inactive position in which the upper side of the platform 18 is below the conveyor belts 12a,b into an active position in which its upper side—with the exception of the recesses 19a,b which then receive the conveyor belts 12a, b—is higher than the latter so that the platform 18 lifts the sample tube rack 7, which in the inactive position of the balance 17 rests on the conveyor belts 12a,b, from the balance 17 when the latter is raised, whereupon the weight of said sample tube rack can be determined.

The centrifuge 2 has a cross 21 which is rotatable about a central axis 20 of rotation and between whose arm four sample tube buckets 22 can be suspended, which buckets are completely or partly filled with sample tubes. The sample tubes are inserted into recesses which are arranged in a plurality of parallel rows in the respective sample tube bucket. The sample tube buckets 22 form two pairs, those belonging to a pair being diametrically opposite one another with respect to the axis 20 of rotation. The weights of the sample tube buckets 22 of a pair may differ from one another by not more than a specific maximum value, which is usually between 15 g and 20 g, in order to limit the imbalance.

The transfer device 3 comprises a gripper 23 (shown in two different positions in FIG. 1) which is suspended in such a way that it can travel in a controlled manner in three directions, in particular in two horizontal directions normal to one another and perpendicularly. It has a downward-projecting gripper clamp 24 which is rotatable about a perpendicular axis in a controlled manner and comprises two gripper fingers 25a,b which are opposite one another and can be moved away from one another or towards one another for, respectively, opening and closing the gripper clamp 24. The gripper fingers 25a,b have, on their end regions, grooved contact surfaces 26 (FIG. 7) which face one another and are covered with a nonslip, resilient coating, for example of polyurethane, for improving the adhesion. The gripper clamp 24 is thus directly suitable for gripping and holding sample tubes 6 and objects of similar shape.

Figure 6:
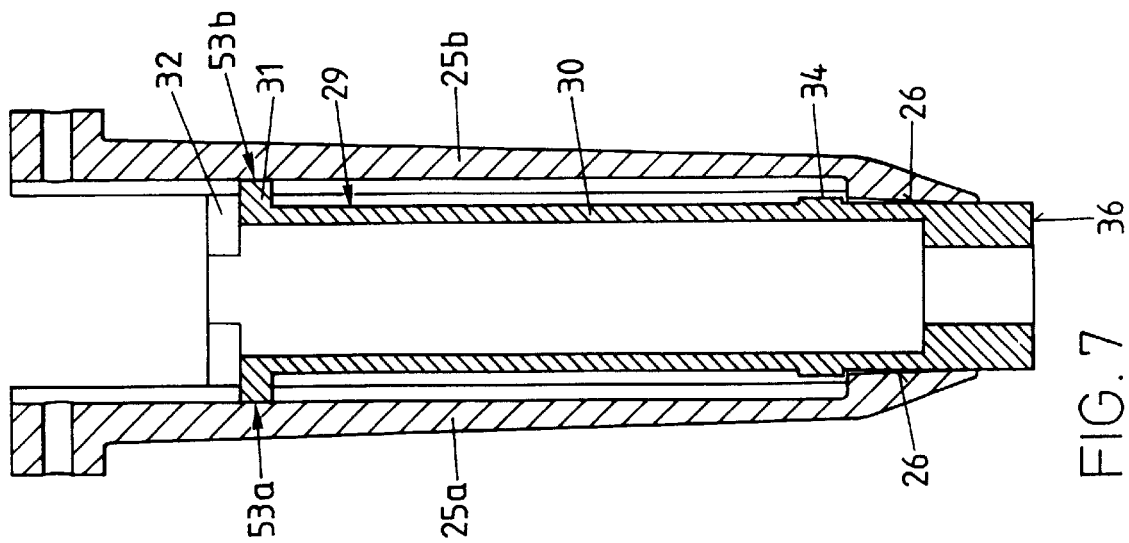
FIG. 6 shows a perspective view of parts of the transfer device according to the invention and FIG. 7 shows a vertical longitudinal section through those parts of the transfer device according to the invention which are shown in FIG. 6.
Figure 7:
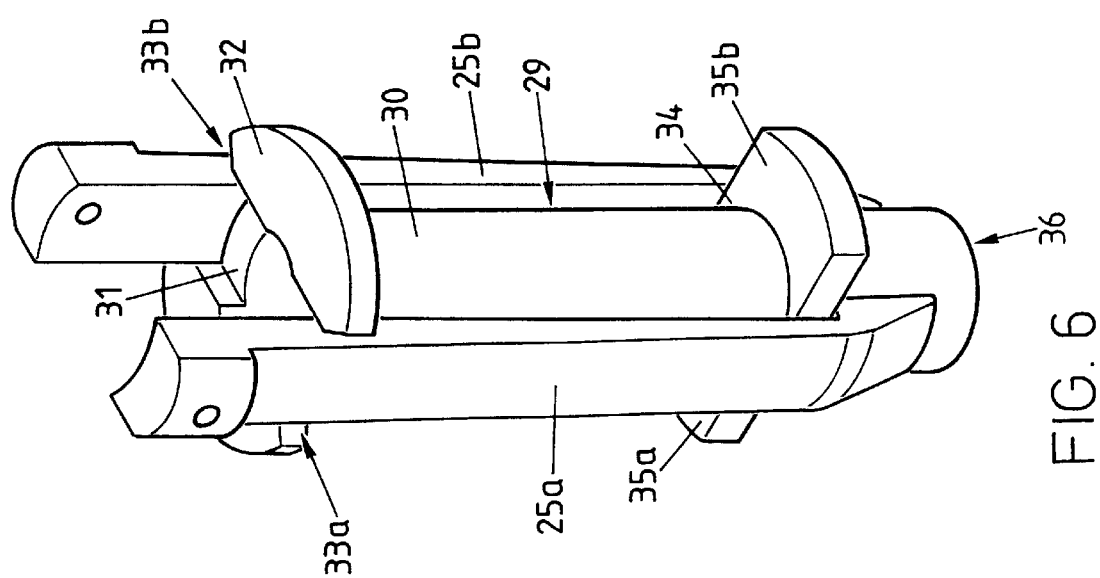

To enable other objects too, such as, for example, sample tube buckets 22, to be gripped by the gripper 23, a receiving device 27 (FIG. 4) is deposited in the access region of said gripper, in a holder 28. The receiving device 27 has an upper handling part 29 which comprises a basic member 30 which is cylindrical, i.e. corresponds in its shape essentially to a sample tube, and carries an all-round first collar 31 at its upper end. Mounted directly above this is a larger second collar 32 which has two recesses 33a,b opposite one another. In the vicinity of its lower end, the basic member 30 carries an elongated third collar 34 which forms two longer extensions 35a,b opposite one another but is only narrow below the recesses 33a,b. The lower end of the basic member 30 forms a downward-pointing annular stop surface 36 (FIGS. 6, 7).

Adjacent to the bottom of the basic member 30 of the handling part 27 is an intermediate part 37 which is connected, for example screwed, to it and has a cylindrical shaft 38 and a support plate 39 which is fastened to its lower end and to the longitudinal sides of which are screwed two U-shaped parts 40a,b, each of which forms two downward-projecting hooks 41 in such a way that the positions of the four identically oriented hooks 41 form the apices of a horizontal rectangle.

The holder 28 has a bottom plate 42 to which is fastened a perpendicular rear wall 43 which carries, slightly below its upper end, a horizontal retaining plate 44 located above the bottom plate 42. Said retaining plate has, at its edge facing away from the rear wall 43, a slot 45 which terminates in a semicircle and is surrounded, on the upper side of the retaining plate 44, by a support strip 46 which forms a ring segment. It is located lower than the surrounding part of the upper side of the retaining plate 44 and is connected to said part via a centring strip 47 inclined inwards in the manner of a funnel. The rear wall 43 is provided with a perpendicular slot 48 which is open at the top, continues through to the retaining plate 44 and has, on its upper edges, bevels 49 sloping downwards in an inward direction. At the front edge, the retaining plate 44 carries two upward-pointing front plates 50a,b which are flush with the rear wall 43 and laterally bound a slightly broader perpendicular slot 51 which is open at the top and likewise has, on its upper edges, bevels 52 sloping downwards in an inward direction.

When the receiving device 47 is placed in the holder 28, the slot 45 receives the shaft 38 of the intermediate part 37 while the stop surface 36 on the lower end of the handling part 29, tightly surrounded by the centring strip 47, rests on the support strip 46. The extensions 35a,b project with little lateral play into the slots 48 and 51, respectively. The three-dimensional position of the receiving device 27 is thus exactly defined, including its rotational position.

If the handling part 29 is held by the gripper clamp 24, the grooved contact surfaces 26 of the gripper fingers 25a,b rest (FIGS. 6, 7), slightly below the third collar 34, against sections of the outside of the cylindrical basic member 30 which form approximately correspondingly convex opposite contact surfaces. The contact surfaces 26 are displaced slightly inwards. The indentations are just below the collar 34 and prevent the handling part 29 from slipping out downwards. The gripper fingers 25a,b are present in the recesses 33a,b in the second collar 32 and form therewith a means for preventing rotation of the handling part 29 about a perpendicular axis as well as for preventing transverse displacement. At the same time, the gripper fingers 25a,b rest with contact regions 53a,b against the outer edge of the first collar 31. Those sections of the gripper fingers 25a,b which are present below the contact area are bent slightly elastically outwards so that the contact surfaces 26 rest against the opposite contact surfaces with a certain contact pressure and fix the basic member 30 immovably there. As a result of the contact of the handling part 29 at two regions a vertical distance apart, said part is also reliably secured to prevent rotations about horizontal axes. The receiving device 27 can thus always be held by the gripper 23 in a defined position and securely guided.

To enable (FIG. 1) the sample tube buckets 22 to be coupled to the receiving device 27, they are provided with four upward-pointing tongues 54 which, in their upper ends, form eyes whose relative position corresponds to that of the hooks 41. The hooks 41 can thus also be introduced into the four eyes for coupling the sample tube bucket 22, whereupon the sample tube bucket 22 can be raised and moved. After said bucket has been set down in the desired place, the hooks 41 can be removed from the eyes.

If it is intended to process a number of samples in the installation according to FIG. 1, in particular if at least some of them are to be centrifuged, a drawer with sample tube racks 7, each of which is completely or partly filled with sample tubes 6, is delivered and is coupled as drawer 16a to the entrance of the feed track 8. The sample tubes 6 each contain samples to be treated and are provided with bar code labels which identify said samples. The sample tube racks 7 are then moved manually onto the feed track 8, picked up there by the conveyor belts and transported further transversely to their longitudinal direction until the feed track 8 has been filled. One sample tube rack 7 after the other is then pushed transversely to the previous transport direction in the longitudinal direction via the intermediate track 10, the sample tubes 6 being assigned one after the other to one of three different classes by the height scanner 13 with respect to their height. Immediately thereafter, the labels of the sample tubes 6 are read by the bar code reader 14 and the samples are further classified with regard to their subsequent processing; inter alia, it is possible on the basis of the bar code to determine whether a sample is to be centrifuged or not.

When the sample tube rack 7 reaches the beginning of the return track 9, it enters the range of action of conveyor belts 12a,b (FIG. 2) of said track, which further transport it, now in a direction opposite to the transport direction of the feed track 8 and once again transversely to its longitudinal direction, until it is present above the balance 17, which is then activated. Said balance is raised until the platform 18 slightly raises the sample tube rack 7 from the conveyor belts 12a,b. The total weight of the sample tube rack 7 is then determined. A first sample tube 6 is then gripped by means of the gripper 23, raised and removed from the sample tube rack 7. The weight of the sample tube rack 7 is then again determined.

If the weight of the removed sample tube 6 is required, which is the case particularly when the sample present in said tube is to be centrifuged, it is determined as the difference between the weights of the sample tube rack 7 determined before and after removal of said tube from the sample tube rack 7. According to the result of the weight determination, the sample tube 6 can then be deposited in one of four sample tube buckets 22 which are present in the access region of the gripper 23. As already explained, a weight distribution is strived for in which the maximum permissible imbalances for the centrifuge 2 are not exceeded. In addition to the weight of the sample tube 6 removed, it is of course also possible to take into account other parameters for the assignment, for example optionally the total weight of the sample tubes 6 remaining in the sample tube rack 7, which can be determined from the last weighing and the known empty weight thereof, or the determined heights of the sample tubes 6. If the sample is not to be centrifuged, the sample tube 6 can be placed directly on one of the carriers 5 of the conveying device 4, with or without determination of the weight of said sample tube.

When further sample tubes 6 are removed, the procedure is exactly the same as that described above. After each removal, the total weight of the sample tube rack 7 is determined and the weight of the sample tube just removed is determined from the difference from the result of the preceding weighing. Once all sample tubes which are to be removed have been removed—usually these are all tubes but it is possible that individual sample tubes are not to be removed, for example if the bar code was not legible—the balance 17 is lowered again to its inactive position and the sample tube rack 7 is further transported, the next one usually simultaneously being moved into the region of the balance 17. At the latest when the return track 9 has been completely filled with—usually empty—sample tube racks 7, the drawer 16b is coupled to the exit of said track, which triggers both lowering of a stop at the end of the return track 9, which previously prevented sample tube racks from being pushed beyond the end of said track, and starting of the conveyor belts 12a,b, which move all sample tube racks 7 from the return track 9 onto the drawer 16b, where, owing to the inclination thereof, they slip outwards until they stop. When it is full, the drawer 16b is uncoupled and removed. The feed device 1 can optionally also be operated so that the sample tube racks are moved from the end of the return track 9 via the second intermediate track 10' back to the beginning of the feed track 8 and thus revolve in a closed circle. In this case, they are manually loaded with sample tubes.

Once the sample tube buckets 22 have been filled, they must be introduced into the centrifuge 2. For this purpose, the gripper 23 approaches the holder 28 (FIG. 4) where the gripper clamp 24 grips the handling part 29, raises it and pulls out the receiving device 27 in a forward direction. Thereafter, a first sample tube bucket 22 in the centrifuge 2 is gripped by a procedure in which the receiving device 27 is positioned by means of the gripper 23 so that the hooks 41 are present in front of the eyes in the tongues 54, whereupon the hooks 41 are introduced into the eyes by a horizontal displacement. The gripper 23 is then raised so that the hooks 41 securely engage the eyes. The sample tube bucket 22 coupled in this manner can now be raised out of the centrifuge 2 and moved to a suitable place. Thereafter, the receiving device 27 is disconnected from the sample tube bucket 22 by a movement sequence opposite to that described above. In a corresponding manner, one of the newly filled sample tube buckets 22 is then moved to the centrifuge 2 and introduced into said centrifuge. Finally, all four sample tube buckets 22 in the centrifuge 2 are thus replaced, the axis 20 of rotation performing in each case a quarter of a rotation before the replacement of a further sample tube bucket 22, so that the removal and introduction of the sample tube buckets into the centrifuge 2 always takes place at the same point.

The gripper 23 then again approaches the holder 28 and deposits the receiving device 27 there. The centring strip 47 and the bevels 49 and 52 ensure that, even when deposition is not very precise, the receiving device 27 exactly assumes its defined position where it can be picked up again securely and without difficulties.

The gripper 23 again immediately removes, by means of the gripper clamp 24, a sample tube 6 from one of the sample tube buckets 22 removed from the centrifuge 2 and places it, for example, on one of the carriers 5 of the conveying device 4. From there, it is then moved to the sample tube rack 7 which is present on the balance 17 and removes from said sample tube rack a sample tube 6 which it then brings, in the manner already described further above, to a sample tube bucket 22 and deposits it there. This process is repeated until all sample tubes 6 in the sample tube buckets 22 have been replaced. At the same time, the samples introduced last into the centrifuge 2 are centrifuged.

The method described and the workstation described can be modified in many details without departing from the scope of the invention.

In particular, the determination of the weight of the sample tubes can also be carried out for purposes other than for the distribution of the said sample tubes over sample tube buckets for centrifuging. The feed device may have further test devices or the ones described can be of another design. Thus, for example, the height scanner may have a different number of cells and the sample tubes may be classified with regard to their height into a number of classes which differs from the height stated in the embodiment. The transfer device may have a plurality of different receiving devices in a plurality of holders which are suitable for coupling to objects of different categories. The workstation may have different modules for distribution, for pipetting and for carrying out other processing steps, all of which are connected to one another by the conveying device and the transfer device—of which there also may be a plurality.

List of Reference Symbols

1 Feed device
2 Centrifuge
3 Transfer device
4 Conveying device
5 Carrier
6 Sample tube
7 Sample tube rack
8 Feed track
9 Return track
10, 10' Intermediate tracks
11 Baseplate
12a,b Conveyor belts
13 Height scanner
14 Bar code reader
15 Recess
16a,b Drawers
17 Balance
18 Platform
19a,b Recesses
20 Axis of rotation
21 Arms
22 Sample tube bucket
23 Gripper
24 Gripper clamp
25a,b Gripper fingers
26 Contact surfaces
27 Receiving device
28 Holder
29 Handling part
30 Basic member
31 First collar
32 Second collar
33a,b Recesses
34 Third collar
35a,b Extensions
36 Stop surface
37 Intermediate part
38 Shaft
39 Support plate
40a,b U-shaped parts
41 Hook
42 Bottom plate
43 Rear wall
44 Retaining plate
45 Slot
46 Support strip
47 Centring strip
48 Slot
49 Bevels
50a,b Front plate
51 Slot
52 Bevels
53a,b Contact regions
54 Tongues

What is claimed is:

1. A method for weighing sample tubes and for loading the sample tubes into sample tube buckets for centrifugation, wherein said sample tubes containing samples of unknown weight and being delivered in sample tube racks, each sample tube rack containing at least one sample tube, and wherein said buckets finally form at least one pair of buckets, the difference of the total weight of the buckets of one of said pairs of buckets in each case being not more than specific maximum value, and wherein the buckets of each pair of buckets are to be introduced into a centrifuge opposite one another with respect to the axis of rotation of the centrifuge, the method for weighing comprising:

a) determining the individual weight of each of said sample containing sample tubes by:
1) placing a sample tube rack, together with at least one sample tube in the rack, on a balance;
2) determining a first total weight of the sample tube rack, together with the at least one sample tube in the rack, with said balance;
3) removing a sample tube from the sample tube rack;
4) determining a second total weight of the sample tube rack, without said removed sample tube, with said balance;
5) calculating the difference of said first and second total weight;
6) assigning said difference as the individual weight to said removed sample tube;

b) loading the sample tubes into the sample tube buckets, according to a weight distribution strived for by:
1) assigning an individual place in a bucket into which a sample tube is inserted according to its individual weight as previously determined by step a);
2) inserting said sample tube into the assigned individual place in the bucket according to its individual weight; and c) repeating steps a) and b) until the buckets of at least one pair of buckets are at least partly filled, the difference of the total weight of the buckets of said pair of buckets being not more than said specific maximum value.

2. The method according to claim 1, wherein each sample tube rack, together with at least one sample tube in the rack, is moved by the action of at least one conveyor belt until it is present above the balance and wherein said balance is raised until its platform raises said sample tube rack from said at least one conveyor belt for weighing said sample tube rack.

3. The method according to claim 1, wherein the total weight of the sample tubes remaining in the sample tube rack is determined from the last weighing and the known empty weight of the rack.

4. The method according to claim 1, wherein the heights of the sample tubes are determined by a height scanner before said sample tubes are removed from the sample tube rack and said sample tubes being assigned to one of three different height classes.

5. The method according to claim 1, wherein the sample tubes comprise bar codes and said bar codes are read by a bar code reader before said sample tubes are removed from the sample tube rack and said sample tubes being assigned to be centrifuged or not.

6. The method according to claim 1, wherein the sample tube buckets are loaded with sample tubes by utilizing a transfer device, said transfer device comprising a gripper with a downward-projecting gripper clamp which comprises two gripper fingers arranged opposite one another.

7. The method according to claim 6, wherein the gripper fingers are equipped, on their end regions, with grooved contact surfaces covered with a non-slip resilient coating.

8. The method according to claim 6, further including the step of introducing two pairs of sample tube buckets into the centrifuge by utilizing said transfer device being equipped with a receiving device that can be gripped by the gripper clamp, each of the buckets being introduced individually into the centrifuge.

9. The method according to claim 8, further including the step of removing the two pairs of sample tube buckets from the centrifuge by utilizing said transfer device being equipped with a receiving device that can be gripped by the gripper clamp, each of the buckets being removed individually from the centrifuge.

10. The method according to claim 8, wherein the steps of inserting the sample tube buckets into the centrifuge and removing the sample tube buckets from the centrifuge always takes place at the same point.

* * * * *